(12) United States Patent
Kumar et al.

(10) Patent No.: US 7,018,510 B2
(45) Date of Patent: Mar. 28, 2006

(54) PROCESS FOR BIO-BLEACHING OF KRAFT PULP USING BACTERIAL CONSORTIA

(75) Inventors: Rita Kumar, New Delhi (IN); Anil Kumar, New Delhi (IN)

(73) Assignee: Council of Scientific and Industrial Research, New Delhi (IN)

(*) Notice: Subject to any disclaimer, the term of this patent is extended or adjusted under 35 U.S.C. 154(b) by 144 days.

(21) Appl. No.: 10/393,353

(22) Filed: Mar. 21, 2003

(65) Prior Publication Data

US 2004/0011485 A1    Jan. 22, 2004

Related U.S. Application Data

(60) Provisional application No. 60/365,840, filed on Mar. 21, 2002.

(51) Int. Cl.
   *D21F 9/10*        (2006.01)
   *C12N 1/00*        (2006.01)

(52) U.S. Cl. ............................ 162/72; 162/60; 162/70; 435/278

(58) Field of Classification Search .................. 162/72, 162/82, 60, 70; 435/42, 410, 243, 253.3, 435/252.34, 253.6, 252.4, 262, 267, 277, 435/278; 424/269.1, 234.1; 210/601, 614, 210/620, 631, 917, 928
See application file for complete search history.

(56) References Cited

OTHER PUBLICATIONS

Frederick S. Archibald, "Lignin Peroxidase Activity Is Not Important in Biological Bleaching and Delignification of Unbleached Kraft Pulp by *Trametes versicolor*", Applied and Environmentl Microbiology, Sep. 1992, pp. 3101-3108, vol. 58-No. 9, American Society for Microbiology.
Brian P. Roy et al., "Effects of Kraft Pulp and Lignin on *Trametes versicolor* Carbon Metabolism", Applied and Environmental Microbiology, Jun. 1993, pp. 1855-1863, vol. 59-No. 6, American Society for Microbiology.
Jośe Cardoso Duarte et al., "Aspergilli and lignocellulosics: Enzymology and biotechnological applications", FEMS Microbiology Reviews, 1994, pp. 377-386, vol. 13, Elsevier.
María Teresa Moreira et al., "Role of Organic Acids in the Manganese-Independent Biobleaching System of *Bjerkandera* sp. Strain BOS55", Applied and Environmental Microbiology, Jul. 1998, pp. 2409-2417, vol. 64-No. 7, American Society for Microbiology.
K. Haider et al., "Screening for Lignin Degrading Bacteria by Means of $^{14}$C-Labelled Lignins", Archives of Microbiology, Oct. 1978, pp. 103-106, vol. 119-No. 1, Springer International.

Ajit Varma et al., "Lignocellulose degradation by microorganisms from termite hills and termite guts: A survey on the present state of art", FEMS Microbiology Reviews, 1994, pp. 9-28, vol. 15, Elsevier.
M. M. Berrocal et al., "Solubilisation and mineralisation of [$^{14}$C]lignocellulose from wheat straw by *Streptomyces cyaneus* CECT 3335 during growth in solid-state fermentation", Appl. Microbiol. Biotechnol., 1997, pp. 379-384, vol. 48, Springer-Verlag.
Ian D. Reid, "Effects of Nitrogen Supplements on Degradation of Aspen Wood Lignin and Carbohydrate Components by *Phanerochaete chrysosporium*", Applied and Environmental Microbiology, Mar. 1983, pp. 830-837, vol. 45-No. 3.
O.K. Beg et al., "Microbial xylanases and their industrial applications: a review", Appl. Microbiol. Biotechnol., 2001, pp. 326-338, vol. 56, Springer-Verlag.
J.H. Clarke et al., "A comparison of enzyme-aided bleaching of softwood paper pulp using combinations of xylanase, mannanase and α-galactosidase", Appl. Microbiol. Biotechnol., 2000, pp. 661-667, vol. 53, Springer-Verlag.
N. Gupta et al., "A Thermostable Extracellular Xylanase from Alkalophilic *Bacillus* sp. NG-27", Biotechnology Letters, Nov. 1992, pp. 1045-1046, vol. 14-No. 11.
Michael J. Bailey et al., "Interlaboratory testing of methods for assay of xylanase activity", Journal of Biotechnology, 1992, pp. 257-270, vol. 23, Elsevier Science Publishers.
Toshiya Sasaki et al, "New Pulp Biobleaching System Involving Manganese Peroxidase Immobilized in a Silica Support with Controlled Pore Sizes", Applied and Environmental Microbiology, May 2001, pp. 2208-2212, vol. 67-No. 5, American Society for Microbiology.
Tamara Vares et al., "Secretion of Ligninolytic Enzymes and Mineralization of $^{14}$C-Ring-Labelled Synthetic Lignin by Three *Phlebia tremellosa* Strains", Applied and Environmental Microbiology, Feb. 1994, pp. 569-575, vol. 60-No. 2, American Society for Microbiology.

(Continued)

*Primary Examiner*—Eric Hug
(74) *Attorney, Agent, or Firm*—Foley & Lardner LLP

(57) ABSTRACT

The present invention relates to an environment friendly, safe, and efficient four-step method of bio-bleaching Kraft pulp using bacterial strains of accession no. MTCC 5096, MTCC 5094, MTCC 5095, and MTCC 5098, a microbial consortium comprising a synergistic mixture of ligninolytic bacterial isolates of accession no. MTCC 5094, MTCC 5095, and MTCC 5098, bacterial strains of accession Nos. MTCC 5096, MTCC 5094, MTCC 5095, and MTCC 5098, and a process of preparing an inoculum of the bacterial isolate of accession no. MTCC 5096, further, a process for the preparation of a consortium comprising the ligninolytic bacterial isolates of accession nos. MTCC 5094, MTCC 5095, and MTCC 5098, in addition, a process for the preparation of pulp suspension for the bio-bleaching.

6 Claims, No Drawings

OTHER PUBLICATIONS

Ryuichiro Kondo et al., "Bleaching of Hardwood Kraft Pulp with Manganese Peroxidase Secreted from *Phanerochaete sordida* YK-624", Applied and Environmental Microbiology, Dec. 1994, pp. 4359-4363, vol. 60-No. 12, American Society for Microbiology.

J. Sealey et al., "Residual lignin studies of laccase-delignified kraft pulps", Enzyme and Microbial Technology, 1998, pp. 422-426, vol. 23, Elsvier Science Inc.

U.S. Appl. No. 10/393,368, filed Mar. 21, 2003, entitled "A Process for the Isolation and Acclimatization of Bacteria for Lignin Degradation".

PROCESS FOR BIO-BLEACHING OF KRAFT PULP USING BACTERIAL CONSORTIA

CROSS REFERENCE TO RELATED PATENTS AND PATENT APPLICATIONS

The present application claims the benefit of provisional application No. 60/365,840, filed Mar. 21, 2002.

FIELD OF THE INVENTION

The present invention relates to an environment friendly, safe, and efficient four-step method of bio-bleaching Kraft pulp using bacterial strains of accession no. MTCC 5096, MTCC 5094, MTCC 5095, and MTCC 5098, a microbial consortium comprising a synergistic mixture of ligninolytic bacterial isolates of accession no. MTCC 5094, MTCC 5095, and MTCC 5098, bacterial strains of accession Nos. MTCC 5096, MTCC 5094, MTCC 5095, and MTCC 5098, and a process of preparing an innoculum of the bacterial isolate of accession no. MTCC 5096, further, a process for the preparation of a consortium comprising the ligninolytic bacterial isolates of accession nos. MTCC 5094, MTCC 5095, and MTCC 5098, in addition, a process for the preparation of pulp suspension for the bio-bleaching.

BACKGROUND AND PRIOR ART REFERENCES

The process of lignin removal from chemical pulps to produce bright or completely white finished pulp is called 'Bleaching'. It is necessary for aesthetic reasons and for improvement of paper properties, because the left over residual lignin after pulping imparts an undesirable brown color to paper. The present day bleaching of Kraft pulp uses large amounts of chlorine based chemicals. The use of these chemicals generates chlorinated organics, which being highly toxic cause various health hazards. Thus, an alternative and cost effective method i.e. the use of microbes and enzymes, has provided a very simple and economic way to reduce the use of chlorine and other bleaching chemicals.

Overview of the Various Organisms

Fungi

Lignin is the most abundant aromatic polymer in the biosphere. It is found in the cell wall of all vascular plants in association with cellulose and hemicellulose. Because inter-unit bonds in lignin are not hydrolysable, lignin is difficult to degrade either chemically or biologically. Lignin surrounds cellulose in the plant cell wall forming a matrix, which is itself resistant to degradation. Lignin biodegradation is responsible for much of the natural destruction of wood in use, and it may have an important role in plant pathogenesis. On the other hand, potential applications utilizing lignin-degrading organisms and their enzymes have become attractive, because they may provide environmentally friendly technologies for the pulp and paper industry. To date, only a few groups of organisms are capable of degrading complex lignin polymers, and they are best exemplified by the white rot fungi. Most of the research concerning biodegradation of lignin has been centered on some fungi only such as *Phanerochaete chrysosporium, Streptomyces viridosporus, Pleurotus eryngii, Trametes trogii, Fusarium proliferatum* (Regaldo et al., 1997) etc. (1).

Wood-rotting basidiomycetous fungi that cause white rot in wood are the most efficient lignin degraders in nature (Kirk and Farrell, 1987; Eriksson et al., 1990), and they are perhaps nature's major agents for recycling the carbon of lignified tissues. No other microorganisms as pure culture have been described to mineralize lignified tissues as efficiently (Kirk and Cullen, 1998). They are a group of taxonomically heterogeneous higher fungi, characterized by their unique ability to depolymerize and mineralize lignin using a set of extracellular lignnolytic enzymes. Lignin degradation by white-rot fungi has been intensively studied during the last thirty years in relation to biotechnical applications such as biopulping, biobleaching, treating of pulp mill effluents, and soil bioremediation (Akhtar et al., 1992, 1998; Lamar et al., 1992; Messner and Srebotnik, 1994).

In 1992, Frederick Archibald (2) demonstrated that the fungus, *Trametes versicolor* was capable of substantial decolorization and delignification of unbleached industrial kraft pulps over 2 to 5 days.

A year later, same group of workers demonstrated that a biobleaching culture supernatant contained all components necessary for hard wood Kraft pulp (HWKP) biobleaching and delignification, but the supernatant needed frequent contact with the fungus to maintain these activities. Thus, labile small fungal metabolites may be the vital Biobleaching system components renewed or replaced by the fungus. Nearly all the $CO_2$ evolved by HWKP containing cultures came from the added glucose, indicating that HWKP is not an important source of energy during Biobleaching. The presence of HWKP in culture markedly increased the culture's production of a number of acidic metabolites, including oxalate, glyoxylate and glycolate.

*Aspergilli*, the versatile ascomycetes are also found to transform at a rapid rate a wide spectrum of lignin related aromatic compounds. They are shown to overproduce high levels of hemicellulolytic enzymes. (4).

Maria Teresa et al. have shown that *Bjerkandera* sp. Strain BOS55 is a white rot fungus that can bleach EDTA extracted eucalyptus oxygen delignified Kraft pulp (UKP) without any requirement for manganese. Furthermore, under manganese free conditions, addition of simple physiological organic acids (e.g. Glycolate, glyoxylate, oxalate and others) at 1–5 mM stimulated brightness gains and pulp delignification two to three fold compared to results not receiving acids. The stimulation was attributed to increase production of MnP and LiP as well as increased physiological concentrations of veratryl alcohol and oxalate. These factors contributed to greatly improved production of superoxide anion radicals, which may have been accounted for the more extensive biobleaching. (5).

Bacteria

The role of bacteria in lignin biodegradation is still a matter of conjecture. Some workers have demonstrated that either mixed (Sundman et al., 1968) or pure culture of bacteria (Sorensen, 1962) can grow on lignin as a carbon source. *Pseudomonas* spp. was claimed by Kawakami (1976) and Odier and Monties (1977) to degrade plant lignins. Odier and Montis also indicated several other bacterial strains that can use within seven days time more than 50% of the lignin supplied in a mineral medium containing glucose.

Several *Nocardia* and *Pseudomonas* spp. as well as some unidentified bacteria, isolated from lake water containing high loads of waste lignin, were tested for their capacity to release $^{14}CO_2$ from specifically $^{14}C$-labelled dehydropolymer of coniferyl alcohol (DHP) or corn stack lignins. However only some of them could release significant amounts of $^{14}CO_2$ from the labeled lignin. The tested Nocardia spp. was more active than the Pseudomonas spp. and the unidentified bacteria.(6).

Actinomycetes are filamentous bacteria which are found in soil and composts where lignocellulose is decomposed. Several reports provide evidence that several species belonging to the genus Streptomyces are able to degrade lignin. Other lignin degrading Actinomycetes include Thermomonospora mesophila, Actinomadura, Micromonospora with Streptomyces exibiting the highest lignin degrading ability. In most of the studies, the lignin degrading enzyme was produced at higher levels in cultures containing lignocellulose which suggests that an induction mechanism was active.

Ajit Verma et al.(1994) while working on symbiotic relationship between termites and their intestinal microbes concluded that both termite soil and termite gut bacteria play an important role in polymer depolymerization. Gut bacteria have the capacity to degrade cellulosic and hemicellulosic materials more efficiently. Several bacterial isolates which hydrolyze cellulose and hemicellulose have been obtained in pure culture from the termite gut. Some of these are Arthrobacter sp., Bacillus cereus, Clostridium sp., Micrococcus sp., Streptomyces sp., Serratia marcescens. Only a few xylan decomposing bacteria have been obtained from the termite gut (Micrococcus luteuns, Pseudomonas aeruginosa). The question of lignin degradation by termites is intriguing, since much of the termite gut is anaerobic and natural anaerobic mechanisms of lignin degradation are unknown. (7).

Berrocal et al. (1997) have shown that cell free filtrates from streptomyces sp. Grown in solid state fermentation were capable of solubilising up to 20% of the [$^{14}$C] lignin. The activity of two enzymes, extracellular peroxidase and phenol oxidase (laccase) was found to correlate with both solubilisation and mineralisation rates of lignin.(8).

The presence of bacteria in rotted wood often in association with fungi has been the subject of numerous reports. However, their exact role in degradation of wood components is still unclear. While the availability of nutrient nitrogen represses metabolism of synthetic $^{14}$C lignin to $CO_2$ by Phanerochaete Chrysosporium, high levels of organic nitrogen were optimal for lignin degradation by the bacterium Streptomyces badius. (9).

Enzymes are the catalytic cornerstones of metabolism, and as such are the focus of intense worldwide research, not only in biological community, but also with process designers/engineers, chemical engineers, and researchers working in other scientific fields. Since ancient times, enzymes have played a central role in many manufacturing process, such as in the production of wine, cheese, bread etc. The latter half of the twentieth century saw an unprecedent expansion in our knowledge of the use of microorganisms, their metabolic products, and enzymes in a broad area of basic research and their potential industrial applications. Only in the past two decades, however have microbial enzymes been used commercially in the Pulp and Paper industry. (10).

The most common application of enzymes in paper industry is to enhance bleaching. At least 15 patents or patent disclosures dealing with enzymatic treatments to enhance bleaching of Kraft pulps were submitted between 1988 and 1993.

Kraft pulping, also known as sulphate, or chemical pulping, uses sulphur to get fiber out of trees. Kraft pulping uses less than 50% of the tree. The rest ends up as sludge which is burned, spread on land or land filled. A bonus of kraft pulping is that the chemicals can be recycled and re-used in the mill. Another is that kraft fiber is exceptionally strong ("kraft" means "strong" in German). Kraft pulp is usually dark and is often bleached with chlorine compounds.

The Kraft process accounts for 85% of the total pulp production in the United States, and it is the largest component of paper manufacture world-wide. Kraft pulping removes lignin, dissolves and degrades hemicellulose without damaging cellulose Unfortunately, degradation products generated during pulping become trapped in the matrix and impart a brown color to Kraft pulp. Cooking consumes pulping chemicals, and residual xylan (along with covalently-linked degradation products) precipitates on the surfaces of the cellulosic fibers. The chromophores are believed to be composed of residual lignin and carbohydrate degradation products. They are hard to extract because they are covalently bound to the carbohydrate moieties in the pulp matrix. Manufacturers use elemental chlorine ($Cl_2$) and chlorine dioxide ($ClO_2$) to bleach the chromophores, and then they extract the pulp to make white paper. The cost of Cl2 is about $12 to $15 per metric ton of pulp, but because this results in the production of chlorinated aromatic compounds, alternative-bleaching agents such as $O_2$, $ClO_2$ or $H_2O_2$ are employed. These can be several times more expensive than $Cl_2$. Bleaching substantially increases the value of the product, so the additional expense can be justified.

Chlorine bleaching can create environmental problems. Byproducts from using these chemicals are chlorinated organic substances, some of which are toxic, mutagenic, persistent, and bioaccumulate, and cause numerous harmful disturbances in biological systems (Onysko,1993). The available options are oxygen delignification, extended cooking, and substitution of chlorine dioxide for chlorine, hydrogen peroxide, and ozone. But most of these methods involve high capital investment for process change. Thus, an alternative and cost effective method, i.e. use of enzymes has provided a very simple and economic way to reduce the use of chlorine and other bleaching chemicals.

Till now, all the basics and applied research work has centered on fungi only. In case of biobleaching of raw pulp, the application of fungi is not feasible due to its structural hindrance caused by fungal hyphae. Bleaching of pulp using purified enzymes from fungi is not economical as the steps of enzyme purification make the process expensive and lengthy. Hence, there exists a need to develop an economically feasible and effective process for bio-bleaching of pulp.

OBJECTS OF THE PRESENT INVENTION

The main object of the present invention is to provide a process to bleach the hardwood kraft pulp using bacterial isolates through a four-stage process.

Another object of the invention is to provide defined bacterial consortia for the bleaching of the hardwood kraft pulp, which is safe, economical, and efficient.

Another object of the invention is to provide the bacterial strains used in this invention for bio-bleaching of the kraft pulp.

Still another object of the present invention is to develop a method of preparing an inoculum using the strains of the instant Application.

SUMMARY OF THE PRESENT INVENTION

The present invention relates to an environment friendly, safe, and efficient four-step method of bio-bleaching Kraft pulp using bacterial strains of accession no. MTCC 5096, MTCC 5094, MTCC 5095, and MTCC 5098, a microbial consortium comprising a synergistic mixture of ligninolytic bacterial isolates of accession no. MTCC 5094, MTCC 5095, and MTCC 5098, bacterial strains of accession Nos. MTCC 5096, MTCC 5094, MTCC 5095, and MTCC 5098, and a process of preparing an inoculum of the bacterial isolate of accession no. MTCC 5096, further, a process for the preparation of a consortium comprising the ligninolytic bacterial isolates of accession nos. MTCC 5094, MTCC 5095, and MTCC 5098, in addition, a process for the preparation of pulp suspension for the bio-bleaching.

DETAILED DESCRIPTION OF THE PRESENT INVENTION

The present invention relates to an environment friendly, safe, and efficient four-step method of bio-bleaching Kraft pulp using bacterial strains of accession no. MTCC 5096, MTCC 5094, MTCC 5095, and MTCC 5098, a microbial consortium comprising a synergistic mixture of ligninolytic bacterial isolates of accession no. MTCC 5094, MTCC 5095, and MTCC 5098, bacterial strains of accession Nos. MTCC 5096, MTCC 5094, MTCC 5095, and MTCC 5098, and a process of preparing an inoculum of the bacterial isolate of accession no. MTCC 5096, further, a process for the preparation of a consortium comprising the ligninolytic bacterial isolates of accession nos. MTCC 5094, MTCC 5095, and MTCC 5098, in addition, a process for the preparation of pulp suspension for the bio-bleaching.

In still another embodiment of the present invention, wherein an environment friendly, safe, and efficient four-step method of bio-bleaching Kraft pulp using bacterial strains of accession no. MTCC 5096, MTCC 5094, MTCC 5095, and MTCC 5098, said method comprising steps of:
  inoculating the pulp suspension with an inoculum of the bacterial strain MTCC 5096 having xylanase activity as stage one,
  incubating the inoculated pulp for time duration ranging between about 15–20 hours at about 100–120 rpm at about 26–32° C.,
  adding sodium hydroxide and hydrogen peroxide to the inoculated pulp of step (c) for alkali extraction as stage two,
  incubating the at about 65–70° C. for time duration of about 1.5–2.5 hrs,
  filtering the pulp and washing with sterile distilled water,
  suspending the washed pulp in fresh minimal salt medium,
  inoculating the pulp suspension with the consortium comprising ligninolytic bacterial strains of accession no. MTCC 5094, MTCC 5095, and MTCC 5098 as stage three,
  incubating the inoculated pulp of step (g) for a period of about 15–20 hrs at about 100–120 rpm at about 26–32° C. at pH of about 5–9,
  repeating the steps (b) to (e) with alkali extraction as stage 4 to obtain pulp with % brightness of about 17%.

In another embodiment of the present invention, wherein the temperature during $3^{rd}$ stage of bio-bleaching is about 30° C.

In yet another embodiment of the present invention, wherein the pH during $3^{rd}$ stage of bio-bleaching is about 8° C.

In still another embodiment of the present invention, wherein 20–30 mg sodium hydroxide and 200–250 ul hydrogen peroxide are added.

In still another embodiment of the present invention, wherein minimal salt medium (MSM) having about 0.1 to 1.0% glucose.

In still another embodiment of the present invention, wherein the strains of the consortium are in the ratio of 1:1:1.

In still another embodiment of the present invention, wherein a microbial consortium comprising a synergistic mixture of ligninolytic bacterial isolates of accession no. MTCC 5094, MTCC 5095, and MTCC 5098.

In still another embodiment of the present invention, wherein a bacterial strain of accession No. MTCC 5096 useful for bio-bleaching pulp.

In still another embodiment of the present invention, wherein the strain shows bio-bleaching of about 8%.

In still another embodiment of the present invention, wherein a bacterial strain of accession No. MTCC 5094.

In still another embodiment of the present invention, wherein a bacterial strain of accession No. MTCC 5095.

In still another embodiment of the present invention, wherein a bacterial strain of accession No. MTCC 5098.

In still another embodiment of the present invention, wherein a process of preparing an inoculum of the bacterial isolate of accession no. MTCC 5096, said process comprising steps of:
  isolating the bacterial strain,
  culturing the bacterial isolate on the medium containing the soil extract and
  nutrient media,
  inoculating the bacterial isolate,
  incubating and centrifuging the resulting culture after attaining the desired O.D. (1.00–2.00) to obtain the pellet,
  suspending the pellet in phosphate buffer of about 0.03–0.05M at about pH 6.8, and
  obtaining the inoculum.

In still another embodiment of the present invention, wherein the isolate is cultured on the medium containing the soil extract and nutrient media in equal proportions.

In still another embodiment of the present invention, wherein the bacterial isolate is inoculated in minimal salt medium with glucose and incubation is carried out by agitation at 100–120 rpm and at a temperature ranging from 28–34° C.

In still another embodiment of the present invention, wherein the resultant growth is centrifuged at appropriate rpm preferably at 8000–12000 rpm for a period of approximately 20–30 minutes at a temperature of 1–4° C.

In still another embodiment of the present invention, wherein the pellet is suspended in appropriate buffer such as phosphate buffer or tris buffer.

In still another embodiment of the present invention, wherein a process for the preparation of a consortium comprising the ligninolytic bacterial isolates of accession nos. MTCC 5094, MTCC 5095, and MTCC 5098 as claimed in claim 5, said method comprising step of:
  isolating the bacterial strains,
  inoculating the bacterial isolate individually, incubating and growing under defined conditions and mixing them in about equal proportions on the basis of optical density values, and
  centrifuging the resultant suspension to obtain the pellet,
  suspending the pellet in phosphate buffer, and
  obtaining consortium consisting of three bacterial strains.

In still another embodiment of the present invention, wherein the incubation of bacterial isolates is carried out by agitation at approximately 100–120rpm and at 30–35° C. for a period of 16 to 18 hours.

In still another embodiment of the present invention, wherein the incubation of bacterial isolates carried out at a temperature ranging between 30° C.–37° C. for a period of 16–18 hours.

In still another embodiment of the present invention, wherein the resultant microbial consortium is centrifuged at approximately rpm preferably at 8000–12000 rpm for a period of approximately 20–30 minutes of 1–4° C.

In still another embodiment of the present invention, wherein the pellet is suspended in appropriate buffer such as phosphate buffer or tris buffer.

In still another embodiment of the present invention, wherein a process for the preparation of pulp suspension for the bio-bleaching said method comprising steps of:
 autoclaving the wet unbleached pulp at about 12–28 psi for about 15–25 minutes, and
 suspending the autoclaved pulp in a medium comprising minimal salts medium with 0.2% glucose under sterile conditions.

In still another embodiment of the present invention, wherein the 7–10% unbleached pulp is autoclaved.

The relation between local deposition no. and International deposition nos is as given below:
1. CBTCC/51-03-MTCC 5096
2. CBTCC/52-03-MTCC 5094
3. CBTCC/53-03-MTCC 5095
4. CBTCC/54-03-MTCC 5098

Characteristics of Bacteria:

MTCC 5096
 Gram-. rods

MTCC 5094
 Gram-, small rods

MTCC 5095
 Gram-, cocci

MTCC 5098
 Gram-, long rods

The above-stated nos are used interchangeably, however, the claims are strictly restricted to only International depository details.

In still another embodiment of the present invention, wherein the present invention provides a novel biological process to bleach the hardwood kraft pulp. This process involves exclusively the use of bacterial isolate to bleach the pulp. Four-stage process includes inoculation of pulp twice with bacterial isolates at different stages followed by alkali washing. Bacterial isolates used in the present process were isolated from a specific site located in Roorkee, India.

The bacterial isolates CBTCC/51-03, CBTCC/52-03, CBTCC/53-03 and CBTCC/54-03 were deposited on Mar. 5, 2003 at International Depository, Microbial Type Culture Collection & Gene Bank, Institute of Microbial Technology, Sector 39-A, Chandigarh, 160 036 India, a WIPO recognized depository and are respectively designated as MTCC 5096, MTCC 5094, MTCC 5095 and MTCC 5098.

In still another embodiment of the present invention, wherein these bacterial isolates are exhibiting a remarkable capability to bleach the hardwood kraft pulp under defined conditions.

In still another embodiment of the present invention, wherein the bacterial isolates in the present invention have been isolated from a wood workshop situated at Roorkee, India, where saw-dust continually accumulated over the period of 10–12 years.

In still another embodiment of the present invention, wherein the bacterial isolates in the present invention includes xylan degrading bacteria and ligninolytic bacteria, so different enrichment was carried out for both types of bacteria before isolation.

In still another embodiment of the present invention, wherein to improve the yield of xylan degrading bacteria, 5 g of fresh soil from the said site was inoculated in the 500 ml autoclaved flask containing 100 ml soil extract, 0.2% xylan and 50 ul Candid B (antifungal). The enrichment flask was kept at 120 rpm for 96 hours at 30° C.

In still another embodiment of the present invention, wherein in an endeavor of inducing ligninolytic bacteria, 5 g of fresh said soil was inoculated in 500 ml flask containing 100 ml nutrient broth, 100 ml soil extract, 0.3% lignin, 1 mM veratryl alcohol, 1 mM guaicol and 50 ul Candid B. Enrichment flask was kept at 30° C./120 rpm for 96 hrs.

In still another embodiment of the present invention, wherein for the preparation of soil extract, 1 Kg soil was taken and dried at 50° C. for 2 hours. 400 g of dried soil was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask and further use.

In still another embodiment of the present invention, wherein the enriched soil samples were serially diluted in 0.85% saline. 100 ul from each respective dilution was spread onto petriplates containing soil extract, 50% nutrient agar and 0.2% xylan for the xylan degrading bacteria or 0.2% lignin for the the isolation of ligninolytic bacteria. The plates thus obtained were incubated at 30±2° C. for 24–96 hrs in inverted position.

In still another embodiment of the present invention, wherein on the basis of colony morphology and colour, total 60 isolates were selected to check their capabilty for bleaching the hardwood pulp. The single isolated colonies were picked and streaked on fresh plates containing the same medium. The above step was repeated till pure colonies were obtained.

In still another embodiment of the present invention, wherein screening of the isolated cultures for the secretion of extracellular xylanases was done for which different isolates were cultured in MSM and 0.7% xylan at 120 rpm/37° C. Xylanase assay was done after every 24 hrs. For determination of β-xylanase activity, 200 µl isolates culture and 800 µl of 0.7% (wt/vol) xylan were mixed and incubated at 55° C. for 10 min. The reaction was stopped by adding 1.5 ml of 3,5-dinitrosalicyclic acid and the solution was well mixed and then heated in a boiling water bath for 15 min. As a control, 800 µl of xylan was incubated and cooled, and 200 µl of phosphate buffer and 1.5 ml of 3,5-dinitrosalicyclic acid were added to correct for reducing sugars in the substrate solution. Reducing sugar equivalents were measured in both the original and control solutions by measuring optical density at 540 nm (Miller et al. 1960) with D-xylose as the standard. One unit of β-xylanase activity was defined as the amount of enzyme that produced 1 µmol of reducing sugar per minute under the given conditions.

In still another embodiment of the present invention, wherein to check the ligninolytic activity of the isolated bacteria, 10 ml of 0.4% lignin was taken in 30 ml test tubes and single bacterial isolate was inoculated. After 3 days, decolorization of lignin was observed.

In still another embodiment of the present invention, wherein bleaching of hardwood kraft pulp using isolated bacteria was carried out in four stages. In the first stage, xylanase secreting bacterial isolate was used while second stage involved the washing with alkali. Third stage included the use of ligninolytic bacteria followed by alkali extraction in fourth stage.

In still another embodiment of the present invention, wherein unbleached hardwood kraft pulp was taken from Century Paper Mill, India. 7 g of wet autoclaved pulp was dissolved in 100 ml autoclaved minimal salt medium (MSM) with 0.3% glucose in 250 ml sterilized flask. Xylanase positive bacterial isolate having 1.00 O.D. was inoculated in 1:5 ratio. The above said bleaching flask was kept at 28° C./120 rpm for 20 hours. After 20 hours incubation, 30 mg sodium hydroxide (NaOH) and 250 ul hydrogen peroxide ($H_2O_2$) were added and the flask was kept at 70° C. for 2 hours. Pulp was filtered using simple whatman paper and again suspended in fresh 100 ml MSM with 0.3% glucose in sterile conditions. The consortium comprising three ligninolytic bacteria was added in 1:5 ratio and the flask was kept at 30° C./120 rpm for 20 hrs. Again alkali extraction was done by adding 30 mg NaOH and 250 ul H2O2 followed by 2 hours incubation at 70° C. Pulp was filtered and suspended in fresh 100 ml triple distilled water. Same experimention was carried out for the control flask having no bacteria.

The invention further provides a four stage process to bleach the hardwood kraft pulp using the bacteria isolated from specific site, which comprises:
a) culturing the said bacteria isolated from specific site under defined conditions such as media, temperature, pH, carbon source etc.;
b) maintaining the density of bacterial culture for the different stages of bleaching process. MSM having 1.0% glucose was used to grow the culture in 250 ml flask having 100 ml culture. The culture flask was incubated at 30° C./120 rpm for 16–18 hours in order to obtain the O.D equal to 1.00;
c) centrifuging the resulting culture after attaining the desired O.D. (1.00), to obtain the pellet;
d) dissolving the above pellet in 20 ml $PO_4^{-3}$ buffer, 0.05M, pH 6.8;
e) preparing of pulp in MSM having 0.3% glucose. 7 g of fresh unbleached pulp is dissolved in 250 ml flask having 100 ml minimal salts medium;
f) inoculating the pulp with xylanase specific bacterial pellet as formed in (d) and incubating the flask at 28° C./120 rpm for 20 hours;
g) adding 30 mg sodium hydroxide and 250 ul hydrogen peroxide in the flask mentioned in (f) and 2 hours incubation at 70° C.;
h) washing and filtering the pulp using simple whatman paper;
i) suspending the washed pulp in fresh 100 ml MSM with 0.3% glucose and 1 mM veratryl alcohol;
j) inoculating the consortium comprising three ligninolytic bacteria as prepared in (b), (c) and (d) and 20 hours incubation at 30° C./120 rpm;
k) adding 30 mg sodium hydroxide and 250 ul hydrogen peroxide in the flask mentioned in (f) and 2 hours incubation at 70° C. as in (g);
l) washing and filtering the pulp using simple whatman paper;
m) drying the pulp at 50° C. for 5 hours and measuring the brightness.

In an embodiment of the present invention, the bacteria are isolated from specific saw-dust site located in Roorkee, India. Isolation involves defined enrichment and different media for xylanases secreting bacteria and ligninolytic bacteria.

In another embodiment of the present invention, the above said bacterial isolates are cultured in minimal salt medium having 1% glucose and growth is monitored to obtain the desired O.D at 30° C./120 rpm/16–18 hrs.

In another embodiment of the present invention, bacterial culture is centrifuged and suspened in 20 ml $PO_4^{-3}$ buffer, 0.05M, pH 6.8 to make the inoculum for bleaching study.

In further embodiment of the present invention, xylanase is assayed by a known method (Miller et al. 1960).

In another embodiment of the present invention, pulp is prepared in MSM having 0.3% glucose. 7–10 gram of fresh unbleached pulp is dissolved in 250 ml flask having 100 ml MSM.

In another embodiment of the present invention, the pulp is inoculated with xylanase specific bacterial pellet and the flask is kept at 28° C./120 rpm for 20 hours.

In embodiment of the present invention, 20–30 mg sodium hydroxide and 200–250 ul hydrogen peroxide are added in the flask and incubated at 70° C. 2 hours.

In another embodiment of the present invention, washing and filtering of the pulp is carried out using simple whatman paper and the pulp is transferred to fresh 100 ml MSM with 0.3% glucose and 1 mM veratryl alcohol.

In further embodiment of the present invention, ligninolytic consortia comprising three bacterial isolates is added and flask is kept at 30° C./100–120 rpm for two hours.

In another embodiment of the present invention, 20–30 mg sodium hydroxide and 200–250 ul hydrogen peroxide are added in the flask and incubated at 70° C. 2 hours.

In further embodiment of the present invention, washing and filtering of the pulp is carried out using simple whatman paper and the pulp is dried at 50° C. for 5 hours.

EXAMPLE 1

A loop from agar plate of bacterial isolate designated as CBTCC/51-03 was inoculated in 100 ml MSM with 1% glucose. The culture was incubated at 30° C. for 16–24 hours in an incubator shaker at 100–120 rpm. After incubation, optical density was measured at 650 nm. Optical density of the culture was maintained to 1.00 either by diluting or concentrating the bacterial suspension. The culture was centrifuged at 10,000 rpm for 30 minutes at 4° C. The pellet was dissolved in 20 ml phosphate buffer, 0.05M, pH 6.8.

The hardwood pulp suspension is prepared by dissolving 10 g autoclaved wet pulp in 100 ml MSM having 0.2% glucose. 1 ml bacterial pellet as prepared above was inoculated in the pulp and flask was incubated at 35° C. at 100 rpm for 15 hrs. No significant whiteness in the pulp was observed because of the inappropriate temperature and less bacterial inoculum.

EXAMPLE 2

A loop from agar plate of bacterial isolate designated as CBTCC/51-03 was inoculated in 100 ml MSM with 1% glucose. The culture was incubated at 30° C. for 16–24 hours in an incubator shaker at 100–120 rpm. After incubation, optical density was measured at 650 nm. Optical density of the culture was maintained to 1.00 either by diluting or concentrating the bacterial suspension. The culture was centrifuged at 10,000 rpm for 30 minutes at 4° C. The pellet was dissolved in 20 ml phosphate buffer, 0.05M, pH 6.8.

The hardwood pulp suspension is prepared by dissolving 7 g autoclaved wet pulp in 100 ml MSM having 0.2% glucose. 10 ml bacterial pellet as prepared above was inoculated in the pulp and flask was incubated at 35° C. at 100 rpm for 15 hrs. No significant whiteness in the pulp was observed because of the inappropriate temperature and less bacterial inoculum.

EXAMPLE 3

400 ml MSM was inoculated with a loopful culture from agar plate of bacterial isolate designated as CBTCC/51-03. The culture was incubated at 30° C. for 16–24 hours in an incubator shaker at 100–120 rpm. After incubation, optical density was measured at 650 nm. Optical density of the culture was maintained to 1.00 either by diluting or concentrating the bacterial suspension. The culture was centrifuged at 10,000 rpm for 30 minutes at 4° C. The pellet was dissolved in 80 ml phosphate buffer, 0.05M, pH 6.8.

Four flasks of pulp suspension were prepared individually by dissolving 7 g autoclaved wet pulp in 100 ml MSM having 0.2% glucose. 20 ml bacterial inoculum as prepared above was inoculated in each flask. First flask was kept at 22° C. while the second at 28° C., third at 34° C. and fouth at 40° C. Alkali extraction was done for all the flask by incubating the pulp at 70° C. for two hours in the presence of NaOH and $H_2O_2$. The flask kept at 28° C. was more bright (8%) in comparison of other flasks (Table 1).

TABLE 1

Temperature optimization of biobleaching process using -(bacterium name)-

| S. No. | Inoculum | Temperature | Brightness |
|---|---|---|---|
| Ist Flask | 20 ml | 220 C. | 2% |
| IInd Flask | 20 ml | 280 C. | 8% |
| IIIrd Flask | 20 ml | 340 C. | 5% |
| IVth Flask | 20 ml | 400 C. | 3% |

EXAMPLE 4

Bleaching experiment was carried out in four steps. First inoculum was prepared by inoculating a 400 ml MSM with a loopful growth from agar plate of bacterial isolate designated as CBTCC/51-03. Second inoculum was prepared by inoculating the three flask individually having 150 ml MSM with a loopful growth of CBTCC/52-03, CBTCC/53-03 and CBTCC/54-03. All the flasks were incubated at 30° C. for 16–24 hours in an incubator shaker at 100–120 rpm. After incubation, optical density was measured at 650 nm. Optical density of the culture was maintained to 1.00 either by diluting or concentrating the bacterial suspension. First culture was centrifuged separately while the three cultures for making the second inoculum were mixed equally and centifuged together. The pellet of first culture was dissolved dissolved in 80 ml phosphate buffer, 0.05M, pH 6.8 while the pellet of three pooled cultures was dissolved in 90 ml phosphate buffer, 0.05M, pH 6.8.

Eight pulp flask were prepared by dissolving the 7 g wet pulp in each 100 ml MSM having 0.2%. First four flasks were inoculated with 20 ml first inoculum of—bacterium—name. All the flasks were incubated at 28° C./120 rpm for 20 hours. After 20 hours incubation, 30 mg NaOH and 250 ul $H_2O_2$ were added and in each flask and icubated at 70° C. for 2 hours. Pulp was filtered using simple whatman paper and again suspended in fresh four 100 ml MSM flasks with 0.2% glucose in sterile conditions. 20 ml second inoculum (consortium) comprising three ligninolytic bacteria was added to each flask. All the flasks were kept at 35° C./120 rpm for 20 hrs. Again alkali extraction was done by adding 30 mg NaOH and 250 ul $H_2O_2$ followed by 2 hours incubation at 70° C. Pulp was filtered and suspended in fresh 100 ml triple distilled water. Same experimentation was carried out for the control flask having no bacteria. Finally, 10–11% brightness was observed in the test pulp flasks (Table 2)

TABLE 2

Combined effect of a singe bacterium and a consortium of three bacteria in the bleaching experiment.

| S. No. | 1st stage (Single bacterium) | IInd Stage | % Brightness | IIIrd Stage (Consortium of three bacteria) | IVth Stage | % Brightness |
|---|---|---|---|---|---|---|
| 1. | 20 ml inoculum | Alkali Extraction | 8 | 20 ml inoculum | Alkali Extraction | 10 |
| 2. | 20 ml inoculum | | 7 | 20 ml inoculum | | 11 |
| 3. | 20 ml inoculum | | 9 | 20 ml inoculum | | 11 |
| 4. | 20 ml inoculum | | 8 | 20 ml inoculum | | 10 |

EXAMPLE 5

In order to see the effect of pH and temperature on biobleaching study, first inoculum was prepared for sixteen 100 ml pulp flasks. For second inculum, a consortium of three bacteria was also prepared for sixteen flasks. Inoculum was prepared as mentioned in earlier examples.

Total sixteen pulp flasks were prepared by dissolving the 7 g wet pulp in each 100 ml MSM having 0.2%. First four flasks were inoculated with 20 ml first inoculum of bacterial isolate designated as CBTCC/51-03. Flask was incubated at 28° C./120 rpm for 20 hours. After 20 hours incubation, 30 mg NaOH and 250 ul $H_2O_2$ were added and the flask was kept at 70° C. for 2 hours. Pulp was filtered using simple whatman paper and again suspended in four fresh 100 ml MSM with 0.2% glucose in sterile conditions. 20 ml second inoculum (consortium) comprising three ligninolytic bacteria was added to the flask. To see the effect of temeperature, pulp flask were kept at 27° C., 30° C., 33° C. and 37° C. for 20 hrs under shaking condition (120 rpm). Again alkali extraction was done by adding 30 mg NaOH and 250 ul $H_2O_2$ followed by 2 hours incubation at 70° C. Pulp was filtered and suspended in fresh 100 ml triple distilled water. Same experimentation was carried out for the control flask having no bacteria. More brightness was observed at 30° C. (Table 3).

To see the effect of pH on biobleaching study, pulp flasks were adjusted to pH 5, pH 7, pH and pH 9 using different buffers. After pH adjustment, these flasks were inoculated with 20 ml first inoculum of bacterial isolate designated as CBTCC/51-03. Flask was incubated at 28° C./120 rpm for 20 hours. After 20 hours incubation, 30 mg NaOH and 250 ul were added and the flask was kept at 70° C. for 2 hours. Pulp was filtered using simple whatman paper and again suspended in four fresh 100 ml MSM having different pH, 5, 7, 8 and 9. 20 ml second inoculum (consortium) comprising three ligninolytic bacteria was added to the flasks. All the flasks were kept at 30° C./120 rpm for 20 hrs. Again alkali extraction was done by adding 30 mg NaOH and 250 ul $H_2O_2$ followed by 2 hours incubation at 70° C. Pulp was filtered and suspended in fresh 100 ml triple distilled water. Same experimention was carried out for the control flask having no bacteria. 15% brightness of pulp was observed at pH 8 (table 4).

TABLE 3

Optimization of temperature during the third stage of biobleaching experiment

| S. No. | Ist stage (Single bacterium) | Temperature | IInd Stage | % Brightness | IIIrd Stage (Consortium of three bacteria) | Temperature | IVth Stage | % Brightness |
|---|---|---|---|---|---|---|---|---|
| 1. | 20 ml inoculum | 28° C. | Alkali | 7 | 20 ml inoculum | 27° C. | Alkali | 10 |
| 2. | 20 ml inoculum | 28° C. | Extraction | 7 | 20 ml inoculum | 30° C. | Extraction | 13 |
| 3. | 20 ml inoculum | 28° C. | | 8 | 20 ml inoculum | 33° C. | | 11 |
| 4. | 20 ml inoculum | 28° C. | | 7 | 20 ml inoculum | 37° C. | | 11 |

TABLE 4

Optimization of pH in the biobleaching experiment

| S. No. | Ist stage (Single bacterium) | IInd pH Stage | % Brightness | IIIrd Stage (Consortium of three bacteria) | IVth pH Stage | % Brightness |
|---|---|---|---|---|---|---|
| 1. | 20 ml inoculum | 5 Alkali | 5 | 20 ml inoculum | 5 Alkali | 11 |
| 2. | 20 ml inoculum | 7 Extraction | 7 | 20 ml inoculum | 7 Extraction | 13 |
| 3. | 20 ml inoculum | 8 | 10 | 20 ml inoculum | 8 | 15 |
| 4. | 20 ml inoculum | 9 | 6 | 20 ml inoculum | 9 | 10 |

The Main Advantages of the Invention

1. The developed four stage biobleaching process replace the use of chlorine and chlorine dioxide in pulp and paper mill. Thus, there is no generation of toxic chlorinated organics such as dioxin, biphenyl etc.
2. The prepared bacterial suspension and consortium cuts the CD stage of chemical bleaching in pulp mill when they act synergistically.
3. In comparison to chemical bleaching, the developed process is highly economical.
4. The developed biobleaching process is environmentally safe because there is no generation of chlorinated pollutants.
5. The developed process is highly competitive in term of technology, feasibility, and applicability.

References (1) Etienne Odier and Isabelle Artaud, 'Degradation of Lignin'. Prof. Dr. Annele Hatakka, 'Biodegradation of Lignin'.
(2) Frederick S. Archibald, 'Lignin Peroxidase activity is not important in biological bleaching and delignification of unbleached kraft pulp by Trametes versicolor' Appl. and Env. Microbiol., September 1992 p. 3101–3109.
(3) Brian P. Roy and Frederick Archibald, 'Effects of Kraft pulp and lignin on Trametes versicolor carbon metabolism', Appl. and Environmental Microbiol., June 1993, P. 1855–1863.
(4) Daurte J C, Costa-Ferreira M; 'Aspergilli and Lignocellulosics: Enzymology and biotechnological applications', FEMS Microbiol. Rev., March 1994; 13 (2–3):377–86.
(5) Maria Teresa, Gumersindo Feijoo, tuned mester, Pablo Mayorga, Reyes sierra-Alvarez and Jim A. Field.; 'Role of Organic acids in the Manganese independent biobleaching system of Bjerkandera sp. Strain BOS55', Appl. and Env. Microbiol., July 1998, p. 2409–2417.
(6) K. Haider, J, Trojanowski, and V. Sundman, 'Screening for lignin degrading Bacteria by means of [$^{14}$C] labeled lignin' Arch. Microbiol. 119, 103–106 (1978).
(7) Varma A., Koll's B. K., Paul J., Saxena S., Koniig H; Lignocellulose degradation by microorganisms from termite hills and termite guts: A survey on the present state of art. FEMS Microbiology Reviews 15 (1994) 9–28.
(8) M. M. Berrocal. J. Rodriguez. A. S. Ball, M. I. Perez-Lebric. M. E. Alias. 'Solubilization and mineralization of [$^{14}$C] lignocellulose from wheat straw by Streptomyces cyaneus CECT 3335 during growth in solid state fermentation', Appl. Microbiol. Biotechnol (1997) 48:379–384.
(9) Ian D. Reid, 'Effects of Nitrogen supplements on degradation of aspen wood lignin and carbohydrate components by P. chrysosporium', Appl. And Env. Micro, March 1983, p. 830–837.
(10) Q. K. Beg. M. Kapoor. L. Mahajan. G. S. Hoondal, Microbial xylanases and their industrial applications, A Review', Appl. Microbiol. Biotech. (2001) 56:326–328.
(11) J. H. Clarke, K. Davidson, J. E. Rixon, J. R. Halstead, M. P. Fransen. H. J. Gilbert G. P. Hazlewood., 'A comparison of enzyme aided bleaching of softwood paper pulp using combinations of xylanase, mannanase and 2-galactosidase.' Appl. Microbiol. Biotechnol. (2000) 53: 661–667.
(12) Thomas W. Jeffries, 'Enzymatic treatments of pulps: Opportunities for the Enzyme Industry in Pulp and Paper Manufacture'.
(13) N. Gupta, R. M. Vohra and G. S. Hoondal. 'A thermophillic extracellular xylanase from alkalophilic Bacillus sp. NG-27', Biotechnology Letters, vol. 14 No. 11 (November 1992) pp. 1045–1046
(14) Michael J. Bailey, Peter Biely and Kaisa Poutanen, 'Interlaboratory testing of methods for assay of xylanase activity', Journal of Biotechnology, 23 (1992) 257–270.
(15) Toshiya susaki, Tsutomu Kajono, BoLi, Hidehiko Sugiyama, and Harua Takatashi; 'New pulp biobleaching system involving manganese peroxidase immobilized in a silicon support with controlled pore sizes', Appl. and Env. Microbiol. May 2001, p 2208–2212.
(16) Tamara Vares, Outi Niemenmaa and Annele Hatakka, 'Secretion of Lignolytic enzymes and mineralization of $^{14}$C-ring labeled synthetic lignin by three Phlebia tremellosa strains', Appl. and Environmental Microbiol. February 1994 569–573.

(17) Ryuichiro Kondo, Koichi Harazono, and Kokki Sakai; 'Bleaching of hardwood Kraft pulp with Manganese Peroxidase secreted from Phanerochaete sordida YK-624'. *Appl. and Env. Microbiol.* December 1994, p. 4359–4363.

(18) J. C. Rols, G. Goma, C. Fonade. 'Biotechnology and the paper industry, Aerated lagoon for the wastewater treatment'.

(19) J. Sealey and A. J. Ragauskas, 'Residual lignin studies of laccase-delignified Kraft pulps', *Enz. And Micro Tech.* 23: 422–426, 1998.

What is claimed is:

1. A method of bio-bleaching Kraft pulp using bacterial strains of accession no. MTCC 5096, MTCC 5094, MTCC 5095, and MTCC 5098, said method comprising the steps of:
   a. inoculating the pulp suspension with an inoculum of the bacterial strain MTCC 5096 having xylanase activity as stage one,
   b. incubating the inoculated pulp for about 15–20 hours at about 100–120 rpm at about 26–32° C.,
   c. adding sodium hydroxide and hydrogen peroxide to the inoculated pulp of step (b) for alkali extraction as stage two,
   d. incubating the pulp at about 65–70° C. for about 1.5–2.5 hrs,
   e. filtering the pulp and washing with sterile distilled water,
   f. suspending the washed pulp in fresh minimal salt medium,
   g. inoculating the pulp suspension with the consortium comprising ligninolytic bacterial strains of accession no. MTCC 5094, MTCC 5095, and MTCC 5098 as stage three,
   h. incubating the inoculated pulp of step (g) for about 15–20 hrs at about 100–120 rpm at about 26–32° C. at a pH of about 5–9,
   i. repeating the steps (b) to (e) with alkali extraction as stage 4 to obtain pulp with a percent brightness of about 17%.

2. A process as claimed in claim 1, wherein the temperature during the third stage of bio-bleaching is about 30° C.

3. A process as claimed in claim 1, wherein the pH during the third stage of bio-bleaching is about 8.

4. A process as claimed in claim 1, wherein 20–30 mg sodium hydroxide and 200–250 µl hydrogen peroxide are added.

5. A process as claimed in claim 1, wherein minimal salt medium (MSM) has about 0.1 to 1.0% glucose.

6. A process as claimed in claim 1, wherein the strains of the consortium are in the ratio of 1:1:1.

* * * * *